United States Patent [19]

Ghosh et al.

[11] Patent Number: 5,160,526
[45] Date of Patent: Nov. 3, 1992

[54] ALKENE STABILIZERS FOR 3-ISOTHIAZOLONE COMPOUNDS

[75] Inventors: Tirthankar Ghosh, North Wales; John R. Mattox, Perkasie, both of Pa.

[73] Assignee: Rohm and Haas Company, Philadelphia, Pa.

[21] Appl. No.: 795,579

[22] Filed: Nov. 21, 1991

[51] Int. Cl.$^5$ .................. A01N 43/80; C07D 275/00; C07D 275/04
[52] U.S. Cl. ........................ 71/67; 514/372; 514/373; 548/209; 548/213
[58] Field of Search ............... 548/209, 213; 71/67; 514/372, 373

[56] References Cited

U.S. PATENT DOCUMENTS 4,824,957  4/1989  Amick ........................ 548/213

Primary Examiner—Mary C. Lee
Assistant Examiner—MarySusan H. Gabilan
Attorney, Agent, or Firm—Michael B. Fein

[57] ABSTRACT

A method of stabilizing a 3-isothiazolone compound against chemical decomposition comprising introducing a sufficient amount of an alkene to stabilize said 3-isothiazolone compound and a composition comprising 3-isothiazolone and an amount of an alkene sufficient to stabilize said isothiazolone.

20 Claims, No Drawings

ALKENE STABILIZERS FOR 3-ISOTHIAZOLONE COMPOUNDS

I. BACKGROUND OF INVENTION

A. Field of Invention

This invention relates to the field of stabilization of 3-isothiazolone compounds.

B. Description of the Prior Art

3-Isothiazolone compounds are among the most successful commercial biocides but suffer from a problem regarding chemical instability. Many stabilizers and stabilization methods have been proposed and used, among which are those disclosed in patent applications assigned to Rohm and Haas Company.

Metal nitrates (referred to in this field as "salt") have been used to stabilize isothiazolones, but salt stabilization has certain disadvantages. Salt free systems have been proposed by Amick, et al., U.S. Pat. No. 4,824,957, but require certain alcohol solvents. The Amick system has disadvantages in certain systems in which the biocide protects a hydrocarbon because the Amick glycols are not miscible in the hydrocarbon.

II. SUMMARY OF INVENTION

It is an objective of this invention to provide an improved stabilization method for 3-isothiazolone compounds. It is a further objective to provide stabilized compositions comprising 3-isothiazolone compounds and a solvent. A still further objective is to provide stabilization for 3-isothiazolone compounds in systems comprising hydrocarbon solvents.

These objects and others as will become apparent from the following disclosure are achieved by the present invention which comprises in one aspect a method of stabilizing 3-isothiazolone compounds against chemical decomposition comprising introducing a sufficient amount of an alkene to stabilize said 3-isothiazolone compound. In another aspect the invention comprises a composition comprising a 3-isothiazolone compound and an amount of an alkene sufficient to stabilize said 3-isothiazolone compound.

III. DETAILED DESCRIPTION OF THE INVENTION AND THE PREFERRED EMBODIMENTS

Suitable alkenes are linear or cyclic, having at least three carbon atoms, substituted or unsubstituted, for example propylene, butylene, and higher linear alkenes, and cyclic or polycyclic alkenes. Preferred cyclic and bicyclic alkenes are those selected from ($C_5$-$C_7$) cyclo- and ($C_6$-$C_{14}$) bicycloalkenes, optionally substituted with one or more radicals selected from the group consisting of ($C_1$-$C_8$) alkyl, ($C_1$-$C_8$) alkenyl, ($C_1$-$C_8$) alkynyl, and ($C_1$-$C_4$) alkoxy.

The preferred alkenes are norbornene, cyclohexene, and 1-tetradecene. Preferred weight ratios of 3-isothiazolone compound to alkene are about 1:100 to 10:1.

Preferred compositions are "salt-free," i.e., free of metal salts, and free of water. Solvents such as ethyl acetate or hydroxy compounds such as isopropanol, 2-butanol, dipropylene glycol, and hydrocarbons are suitable. Kerosene, xylene, and other aromatic hydrocarbons are also suitable solvents. The solvent should not interfere with the stabilizing action of the alkene. Preferred concentrations of 3-isothazolone are about 0.1 to 20%, more preferably about 1 to 10% by weight. The alkenes can be incorporated by simple addition to the 3-isothiazolone biodide compound, or solutions thereof, in amounts sufficient to stabilize the isothiazolone biocide.

The stabilized isothiazolones can be used in the usual way to inhibit the growth of bacteria, fungi, or algae in the normal way, i.e., by incorporating the compositions into or onto a locus subject to contamination.

The 3-isothiazolone biocide is especially suitable for protecting systems having both an organic and a water phase, e.g., fuel storage tanks, because the biocide is soluble in both phases. The alkenes used in this invention are soluble in the organic phase. An especially suitable locus is motor fuel.

Suitable 3-isothiazolone compounds are those which function as biocidal compounds, generally of the formula

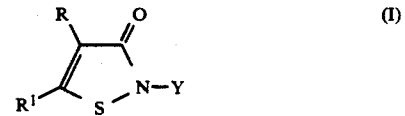

(I)

wherein R and $R^1$ are independently selected from hydrogen, halogen or a ($C_1$-$C_4$) alkyl group or alternatively may be joined to form a saturated, unsaturated or aromatic 5- or 6-membered fused carbocyclic ring; Y is hydrogen, an alkyl or substituted alkyl of 1 to 18 carbon atoms, an unsubstituted or halo-substituted alkenyl or alkynyl of 2 to 8 carbon atoms, a cycloalkyl or substituted cycloalkyl of 3 to 12 carbon atoms, an aralkyl or halo-, ($C_1$-$C_4$) alkyl-, or ($C_1$-$C_4$) alkoxy-substituted aralkyl of up to 10 carbon atoms, or an aryl or halo-, ($C_1$-$C_4$) alkyl-, or ($C_1$-$C_4$) alkoxy-substituted aryl of up to 10 carbon atoms disclosed. Especially suitable 3-isothiazolones are 5-chloro-2-methyl-3-isothiazolone, 2-methyl-3-isothiazolone, and 4,5-dichloro-2-n-octyl-3-isothiazolone.

The following examples are presented to illustrate a few embodiments of the invention.

EXAMPLES

Example 1

5-Chloro-2-methyl-3-isothiazolone + Norbornene in 2-Butanol

Five samples were prepared by dissolving 5-chloro-2-methyl-3-isothiazolone + norbornene in 2-butanol (20:80) and adding different amounts of norbornene. The samples were put in a 55° C. oven and analyzed periodically. Results are shown in Table 1.

TABLE 1

Stabilization of 5-Chloro-2-methyl-3-isothiazolone by Norbornene in 2-Butanol

| Norbornene (%) | % 5-Chloro-2-methyl-3-isothiazolone remaining after | | |
|---|---|---|---|
| | 0 days | 14 days | 34 days |
| 0 | 20.1 | 22.4 | <0.1 |
| 4.2 | 19.0 | 19.2 | 20.1 |
| 7.9 | 18.1 | 18.9 | 19.9 |
| 11.3 | 17.5 | 17.8 | 17.8 |
| 16.0 | 15.8 | 17.6 | 22.8 |

EXAMPLE 2

5-Chloro-2-methyl-3-isothiazolone + Norbornene in 2-Propanol

Two samples were prepared by dissolving 5-chloro-2-methyl-3-isothiazolone in 2-propanol (20:80). One was used as a control and norbornene was added to the other. Both samples were then put in a 55° C. oven and analyzed periodically. It should be noted that the 2-propanol used has trace amounts of water.

TABLE 2

Stabilization of 5-Chloro-2-methyl-3-isothiazolone by Norbornene in 2-Propanol

| Norbornene (%) | 5-Chloro-2-methyl-3-isothiazolone remaining after | | |
|---|---|---|---|
| | 0 days | 14 days | 35 days |
| 0 | 19.4 | 19.5 | <0.1 |
| 8.8 | 16.9 | 17.5 | 17.0 |

EXAMPLE 3

Mixture of 5-Chloro-2-methyl-3-isothiazolone and 2-Methyl-3-isothiazolone + Norbornene in 2-Propanol A solution of a mixture of 5-chloro-2-methyl-3-isothiazolone ("5-Chloro") and 2-methyl-3-isothiazolone ("2-Methyl") (Kathon® SF brand) was prepared in 2-propanol (16.1 g). This solution was distributed into 6 vials and varying amounts of norbornene added. They were then put in a 55° C. oven and analyzed periodically. Results are shown in Table 3.

TABLE 3

Stabilization of 5-Chloro-2-methyl-3-isothiazolone and 2-Methyl-3-isothiazolone by Norbornene in 2-Propanol % Remaining After X Days

| Norbornene (%) | % 2-Methyl | | | % 5-Chloro | | |
|---|---|---|---|---|---|---|
| | 0 days | 2 days | 30 days | 0 days | 2 days | 30 days |
| 0 | 4.9 | 0.4 | 0.7 | 12.3 | 0.5 | <0.1 |
| 3 | 4.7 | 4.4 | 3.9 | 11.8 | 12.4 | 12.8 |
| 6.3 | 4.5 | 4.3 | 4.0 | 11.6 | 11.6 | 11.4 |
| 11.8 | 4.2 | 4.0 | 3.9 | 10.7 | 10.9 | 10.9 |
| 16.7 | 4.0 | 3.9 | 3.7 | 10.1 | 10.4 | 10.3 |
| 21.0 | 3.9 | 3.8 | 3.7 | 9.9 | 10.2 | 10.1 |

Thus both 5-chloro-2-methyl-3-isothiazolone and 2-methyl-3-isothiazolone are completely stabilized with norbornene.

EXAMPLE 4 (COMPARATIVE)

Mixture of 5-Chloro-2-methyl-3-isothiazolone and 2-Methyl-3-isothiazolone + Norbornene in 2-Propanol with 2% added Water A solution of 5-chloro-2methyl-3-isothiazolone ("5-Chloro") and 2-methyl-3-isothiazolone ("2-Methyl") (3.11 g) was prepared in 2-propanol (12.1 g). This solution was distributed in 6 vials. Water (2%) and varying amounts of norbornene were then added. These were then put in a 55° C. oven and analyzed periodically. The results are shown in Table 4.

TABLE 4

Norbornene as a Stabilizer for a Mixture of 5-Chloro-2-methyl-3-isothiazolone and 2-Methyl-3-isothiazolone in a Norbornene + 2-Propanol + Water System

| Norbornene (%) | 2-Methyl (%) | | | 5-Chloro (%) | | |
|---|---|---|---|---|---|---|
| | 0 days | 7 days | 21 days | 0 days | 7 days | 21 days |
| 0 | 1.7 | 0.22 | — | 12.2 | 0.23 | — |
| 1.2 | 2.3 | 0.14 | — | 16.7 | 0.09 | — |
| 2.3 | 2.3 | 0.08 | — | 16.5 | 0.09 | — |
| 4.2 | 2.2 | 0.10 | — | 16.2 | 0.07 | — |
| 8.1 | 2.2 | 0.10 | — | 15.7 | <0.1 | — |
| 14.1 | 2.0 | 0.97 | 0.1 | 14.7 | 13.5 | <0.1 |

These results indicate that the presence of ~2% water in the solution overwhelms the stabilization properties of norbornene. Some stability is realized when an approximately equivalent weight percent of norbornene to AI is used.

EXAMPLE 5

Stabilization of a Mixture of 5-Chloro-2-methyl-3-isothiazolone and 2-Methyl-3-isothiazolone with Norbornene in Dipropylene Glycol containing 0.5% Water To 19.9 g of dipropylene glycol was added 0.1 g of water. To this were added 5-chloro-2-methyl-3-isothiazolone ("5-Chloro") and 2-methyl-3-isothiazolone ("2-Methyl"). This solution was distributed into 6 vials and varying amounts of norbornene were added. The vials were put in a 55° C. oven and analyzed periodically. Results are shown in Table 5.

TABLE 5

Stabilization of a Mixture of 5-Chloro-2-methyl-3-isothiazolone and 2-Methyl-3-isothiazolone with Norbornene in DPG (0.5% water)

| Norbornene (%) | 2-Methyl (%) | | | 5-Chloro (%) | | |
|---|---|---|---|---|---|---|
| | 0 days | 14 days | 30 days | 0 days | 14 days | 30 days |
| 1.6 | 4.4 | 0.18 | — | 11.7 | 0 | — |
| 3.2 | 4.3 | 3.3 | 0.6 | 11.5 | 10.4 | 0.1 |
| 6.5 | 4.2 | 3.7 | 2.7 | 11.2 | 10.8 | 10.1 |
| 9.0 | 4.1 | 3.7 | 3.3 | 11.0 | 10.7 | 10.4 |
| 14.3 | 4.4 | 3.6 | 3.3 | 10.5 | 10.2 | 9.7 |
| 0 | 4.5 | 0.6 | — | 11.7 | 0.0 | 0 |

EXAMPLE 6

Cyclohexene as a Stabilizer for a Mixture of 5-Chloro-2-methyl-3-isothiazolone and 2-Methyl-3-isothiazolone.

A solution of 5-chloro-2-methyl-3-isothiazolone ("5-Chloro") and 2-methyl-3-isothiazolone ("2-Methyl") (3.6 g) was dissolved in 17 g of dipropylene glycol. This solution was distributed into 6 vials (3 g each) and varying amounts of cyclohexene were added. The vials were then heated at 55° C. and analyzed periodically. Results are shown in Table 6.

TABLE 6

Stabilization of a Mixture of
5-Chloro-2-methyl-3-isothiazolone
and 2-Methyl-3-isothiazolone by
Cyclohexene in DPG

| cyclohexene (%) | 2-Methyl (%) | | | 5-Chloro (%) | | |
|---|---|---|---|---|---|---|
| | 0 days | 13 days | 30 days | 0 days | 13 days | 30 days |
| 0 | 5.0 | 0.49 | — | 11.4 | <0.1 | — |
| 3.2 | 4.7 | 0.35 | — | 10.1 | 0.19 | — |
| 6.8 | 4.6 | 0.23 | — | 10.9 | 0.10 | — |
| 9.1 | 4.5 | 0.95 | 0.66 | 10.6 | 8.6 | 0.0 |
| 11.8 | 4.4 | 0.59 | 0.62 | 10.5 | 7.9 | 0.0 |
| 16.7 | 4.3 | 2.6 | 0.46 | 10.2 | 9.0 | 0.0 |

These results indicate that cyclohexene functions as a stabilizer. Since the isothiazolone batch used was already dark in color (later analysis indicated 5% decomposition), the data may not reflect the results expected from a pure batch of starting material.

EXAMPLE 7 (COMPARATIVE)

Attempted Stabilization of a Mixture of
5-Chloro-2-methyl-3-isothiazolone and
2-Methyl-3-isothiazolone with 3,4-Dihydro-2H-pyran
(DHP) in 2-Propanol.

A solution of 5-chloro-2-methyl-3-isothiazolone ("5-Chloro") and 2-methyl-3-isothiazolone ("2-Methyl") (3.6 g) was prepared in 2 propanol (16.1 g) containing water as an impurity and distributed into 6 vials. Varying amounts of DHP were added and the vials put in a 55° C. oven. Active ingredient analysis was done periodically. As the following results (Table 7) indicate, DHP imparts no stability to isothiazolones in alcohol-water systems. It is expected that DHP would stabilize the isothiazolone in hydrocarbon systems such as fuel.

TABLE 7

5-Chloro-2-methyl-3-isothiazolone and
2-Methyl-3-isothiazolone + DHP in 2-Propanol.

| DHP (%) | 2-Methyl (%) | | 5-Chloro (%) | |
|---|---|---|---|---|
| | 0 days | 12 days | 0 days | 12 days |
| 0 | 5.3 | 0.4 | 11.6 | 0.4 |
| 3.5 | 5.1 | 0.7 | 11.1 | 0.1 |
| 6.3 | 5.0 | 0.6 | 10.8 | 0.1 |
| 11.8 | 4.2 | 0.7 | 10.2 | 0.6 |
| 16.7 | 4.4 | 0.7 | 9.7 | 0.5 |
| 21.1 | 4.2 | 0.6 | 9.2 | 0.4 |

EXAMPLE 8 (COMPARATIVE)

Other olefins that were tested but failed to show any stabilizing properties in 2-propanol/water systems were cyclooctene, dicylopentadiene and indene. It is expected that these alkenes would function to stabilize the biocide in non-aqueous systems, however.

EXAMPLE 9

In a formulation comprised of 3 parts by weight of a mixture of 5-chloro-2-methyl-3-isothiazolone and 2-methyl-3-isothiazolone in a 3:1 ratio, 94 parts by weight of a mixture of kerosene (64 parts by weight) and diethylene glycol butyl ether (20 parts by weight), 3 parts by weight norbornene stabilizer was added. The control had no norbornene. After eight weeks at 55° C., the control had no 5-chloro-2-methyl-3-isothiazolone left, whereas the composition of the invention had 100% 5-chloro-2-methyl-3-isothiazolone remaining.

EXAMPLE 10

Example 9 was repeated except using 1 part by weight norbornene. No loss of 5-chloro-2-methyl-3-isothiazolone was observed after eight weeks at 55° C.

EXAMPLE 11

Example 9 was repeated except using 1-tetradecene as stabilizer resulting in 86% 5-chloro-2-methyl-3-isothiazolone remaining after four weeks at 55° C. and complete loss by eight weeks.

Although specific embodiments and examples have been described herein, it should be born in mind that these have been provided by way of explanation and illustration and that the present invention is not limited thereby. Modifications which are within the ordinary skill in the art to make are considered to lie within the scope of the invention as defined by the following claims, including all equivalents.

We claim:

1. A method of stabilizing 3-sothiazolone compounds of the formula $$\underset{R^1}{\overset{R}{\diagdown}}\!\!=\!\!\underset{S}{\overset{O}{\diagup}}\!\!\diagdown_{N-Y} \quad (I)$$

wherein R and $R^1$ are independently selected from hydrogen, halogen or a ($C_1$–$C_4$) alkyl group or alternatively may be joined to form a saturated, unsaturated or aromatic 5- or 6-membered fused carbocyclic ring; Y is hydrogen, an alkyl or substituted alkyl of 1 to 18 carbon atoms, an unsubstituted or halo-substituted alkenyl or alkynyl of 2 to 8 carbon atoms, a cycloalkyl or substituted cycloalkyl of 3 to 12 carbon atoms, an aralkyl or halo-, ($C_1$–$C_4$) alkyl-, or ($C_1$–$C_4$) alkoxy-substituted aralkyl of to 10 carbon atoms, or an aryl or halo-, ($C_1$–$C_4$) alkyl-, or ($C_1$–$C_4$) alkoxy-substituted aryl of up to 10 carbon atoms; against chemical decomposition comprising introducing a sufficient amount of an alkene having at least three carbon atoms to stabilize said 3-isothiazolone compound.

2. Method according to claim 1 wherein the weight ratio of isothiazolone to alkene is about 1:100 to 10:1.

3. Method according to claim 1 wherein said alkene is selected from the group consisting of ($C_5$–$C_7$) cyclo- and ($C_6$–$C_{14}$) bicycloalkenes, optionally substituted with one or more radicals selected from the group consisting of alkyl ($C_2$–$C_8$) alkenyl, ($C_2$–$C_8$) alkynyl, and ($C_1$–$C_4$) alkoxy.

4. The method of claim wherein said alkene is selected from the group consisting of norbornene, cyclohexene, cyclohexadiene, and tetradecene.

5. A composition comprising a 3-isothiazolone compound of the formula $$\underset{R^1}{\overset{R}{\diagdown}}\!\!=\!\!\underset{S}{\overset{O}{\diagup}}\!\!\diagdown_{N-Y} \quad (I)$$

wherein R and $R^1$ are independently selected from hydrogen, halogen or a ($C_1$–$C_4$) alkyl group or alternatively may be joined to form a saturated, unsaturated or aromatic 5- or 6-membered fused carbocyclic ring; Y is hydrogen, an alkyl or substituted alkyl of 1 to 18 carbon atoms, an unsubstituted or halo-substituted alkenyl or alkynyl of 2 to 8 carbon atoms, a cycloalkyl or substituted cycloalkyl of 3 to 12 carbon atoms, an aralkyl or halo-, ($C_1$-$C_4$) alkyl- or ($C_1$-$C_4$) alkoxy-substituted aralkyl of to 10 carbon atoms, or an aryl or halo-, ($C_1$-$C_4$) alkyl-, or ($C_1$-$C_4$) alkoxy-substituted aryl of up to 10 carbon atoms; and an amount of an alkene having at least three carbon atoms sufficient to stabilize said 3-isothiazolone compound.

6. A composition according to claim 5 wherein said alkene is selected from the group consisting of norbornene, cyclohexene, cyclohexadiene, and tetradecene.

7. A composition according to claim 5 wherein said alkene selected from ($C_5$-$C_7$) cyclo- and ($C_6$-$C_{14}$) bicycloalkenes, optionally substituted with one or more radicals selected from the group consisting of ($C_1$-$C_8$) alkyl ($C_2$-$C_8$) alkenyl, ($C_2$-$C_8$) alkynyl, and ($C_1$-$C_4$) alkoxy.

8. A composition according to claim 5 free of metal salts.

9. A composition according to claim 5 further including a solvent which does not interfere with the stabilizing action of said alkene.

10. A composition according to claim 5 wherein said solvent is selected from the group consisting of isopropanol, 2-butanol, dipropylene glycol, ethyl acetate, and hydrocarbon.

11. A composition according to claim 10 wherein said solvent is a hydrocarbon selected from the group consisting of kerosene and an aromatic hydrocarbon.

12. A composition according to claim 5 wherein the weight ratio of 3-isothiazolone to alkene is about 1:1 to 5:1.

13. A composition according to claim 5 wherein said 3-isothiazolone is selected from the group consisting of 5-chloro-2-methyl-3-isothiazolone, 2-methyl-3-isothiazolone, and 4,5-dichloro-2-n-octyl-3-isothiazolone.

14. A method for inhibiting the growth of bacteria, fungi, or algae in a locus subject to contamination by bacteria, fungi, or algae, which comprises incorporating into or onto said locus, in an amount which is effective to adversely affect the growth of bacteria, fungi, or algae, sufficient amount of the composition of claim 5.

15. The method of claim 14 wherein said locus is an aqueous medium.

16. The method of claim 14 wherein said locus is a cosmetic formulation.

17. The method of claim 14 wherein said locus is fabric, leather, paper, or wood.

18. The method of claim 14 wherein said locus is a solid protective or decorative film.

19. Method of claim 14 wherein said locus is a fuel composition which comprises water as impurity.

20. A composition according to claim 5 wherein said solvent is xylene.

* * * * *